United States Patent [19]

Knapp et al.

[11] Patent Number: 5,782,806
[45] Date of Patent: Jul. 21, 1998

US005782806A

[54] MEDICAL EVACUATION AND IRRIGATION SYSTEM

[75] Inventors: Michael N. Knapp; Woodrow W. Watson; Richard H. Radcliff, all of Flagstaff, Ariz.

[73] Assignee: W. L. Gore & Associates, Inc., Newark, Del.

[21] Appl. No.: 711,430

[22] Filed: Sep. 6, 1996

[51] Int. Cl.⁶ .................................................. A61M 5/20
[52] U.S. Cl. .......................... 604/131; 604/247; 604/248; 604/257
[58] Field of Search .................................. 604/131, 151, 604/246, 247, 248, 257, 19, 27, 30, 48

[56] References Cited

U.S. PATENT DOCUMENTS

| | | | |
|---|---|---|---|
| 4,428,383 | 1/1984 | De Vroom | 604/248 X |
| 4,529,397 | 7/1985 | Hennemuth et al. | 604/27 X |
| 5,034,000 | 7/1991 | Freitas et al. | |
| 5,100,377 | 3/1992 | Freitas et al. | |
| 5,382,229 | 1/1995 | Grabenkort | 604/27 |
| 5,505,707 | 4/1996 | Manzie et al. | 604/247 X |
| 5,514,089 | 5/1996 | Walbrink et al. | |
| 5,520,638 | 5/1996 | O'Quinn et al. | |

FOREIGN PATENT DOCUMENTS

0199876 A2  11/1986  European Pat. Off.

OTHER PUBLICATIONS

McCaughan, John J., et al. In Vitro observations of greater saphenous vein valves during pulsatile and nonpulsatile flow and following lysis. J Vasc Surg. 1984; 1:356–61.

*Primary Examiner*—Kien T. Nguyen
*Assistant Examiner*—Benjamin K. Koo
*Attorney, Agent, or Firm*—Wayne D. House; Gregory J. Nelson

[57] ABSTRACT

An irrigation system for use primarily with in situ bypass and valvulotomy procedures. The system includes access to both the proximal and distal ends of a length of vein and allows for irrigation flow to be provided from proximal to distal, distal to proximal or to both proximal and distal ends of the vein simultaneously. The use of the irrigation system provides for a clear field of view by angioscope during medical procedures. Introducers are also described which may be used with the irrigation system or with many other procedures which require access to an internal body conduit.

10 Claims, 6 Drawing Sheets

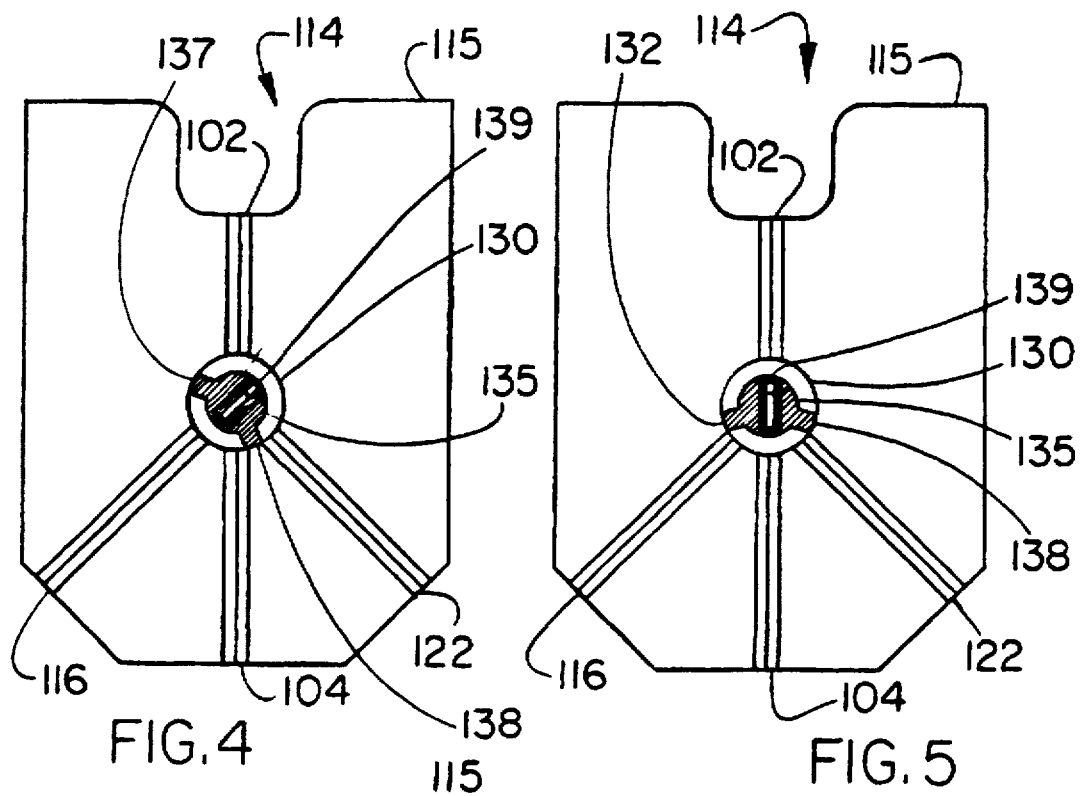
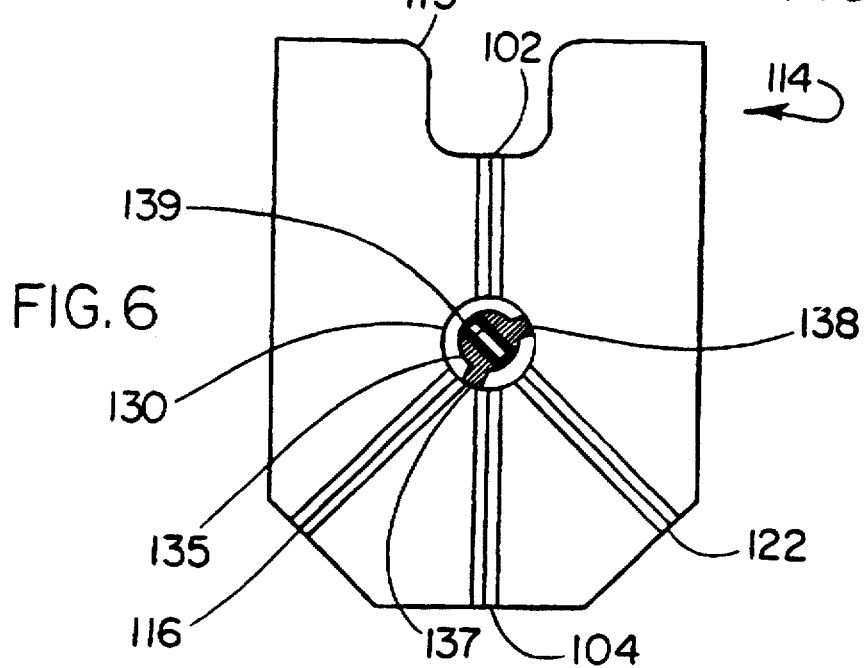

5,782,806

MEDICAL EVACUATION AND IRRIGATION SYSTEM

FIELD OF THE INVENTION

This invention relates to medical devices and more particularly to an irrigation system which provides improved visualization of a vein, artery or other surgical site by clearing the viewed area of obscuring blood and tissue when conducting procedures such as laparoscopic and angioscopic surgery.

BACKGROUND OF THE INVENTION

Current angioscopic techniques for distal extremity artery bypass surgery typically employ an angioscope and an introducer sheath. The introducer sheath is inserted into a proximal cut end of the vein near the groin area providing the surgeon a location for insertion of the angioscope and allows the surgeon to view the vein as the angioscope proceeds towards the ankle. Alternately, the angioscope may be inserted through a large side branch at the proximal end of the vein. Angioscopic visualization is employed to verify the disruption of the venous valves and to identify the location of venous tributaries.

Several patents disclose devices for providing irrigation and evacuation during surgery. U.S. Pat. Nos. 5,034,000 and 5,100,377 both disclose devices for providing irrigation and evacuation during laparoscopic surgery which devices include valve arrangements to prevent reflux of fluid and the drawing of irrigation fluid from a reservoir in the event the patient line becomes blocked. These devices are intended primarily for use in connection with laparoscopic surgery and assist the surgeon in obtaining an unobstructed view of the surgical site.

Several devices are also available for use in connection with angioscopic valvulotomies which may be inserted at the distal end of a vein to provide a flow of irrigation fluid. Representative of these devices are the Intramed Angioscopic Valvulotome (manufactured by Baxter) and the Applied Medical Angioscopic Valvulotome System. However, these devices, while effective, do not accommodate reversible irrigation and do not provide venting to a collection system. Further, prior art systems of this type experience difficulty in expeditiously clearing and maintaining the field of view and do not permit simultaneous irrigation flow into opposite ends of a vein and do not provide for hydraulic pressure regulation. Likewise, prior art systems do not quickly clear the field of view using a minimal amount of fluid, nor do they monitor the volume of fluid infused.

SUMMARY OF THE INVENTION

The present invention provides an angioscopic irrigation manifold system (AIMS) which includes proximal and distal introducer sheaths with a sealing port orifice. In use, the system expedites clearing of the field of view, minimizes bolus infusion volume to the patient and reduces hydraulic pressure to the vein.

The system includes a tubing set having at least one fluid control valve for irrigating and venting fluid from a surgical location such as a vein when performing an in situ saphenous vein bypass. While two valves may be used, it is preferred that the valve functions are integrated in a single control valve body having an inlet port connected to a fluid pressure source such as an infusion pump and outlet ports connected by appropriate tubing to proximal and distal introducer sheaths which may be inserted, as for example, at the proximal and distal ends of the saphenous vein. The valve also has an outlet port connected to a collection bag. The valve is a multiple position valve that may be operated to introduce irrigation fluid at either the proximal or distal location with venting directed to the collection bag from the opposite end of the vein. The valve, when positioned to direct irrigation flow distally to proximally in an occluded saphenous vein, allows clearing of the entire field of view prior to valvulotomy to inspect for tributary and venous valve locations and tortuosities. The valve may also be put in a bi-directional position, in which irrigation fluid is simultaneously directed to both the distal and proximal locations which provides equalized irrigant pressure across tributaries for better maintenance of view. In another position, the valve when used during valvulotomies, controls irrigation fluid so that it can be directed to the proximal introducer sheath location and returned from the distal end to the collection bag or container, thereby closing the venous valves for disruption. Minimal bolus infusion volume to the patient reduces cardiac and renal stress.

A pre-set pressure limiting control may also be incorporated into the valve body to prevent over-pressurization of the vein and tributaries.

In addition, the present invention provides an intravenous introducer sheath which has an expandable introducer tip which may be calibrated and is adjustable to allow the tip to be expanded in diameter between a range of approximately two to eight millimeters to correspond to the desired French diameter. The introducer sheath also has a hemostatic seal and a tubular sleeve which protects the seal from the surfaces of sharp tools during insertion into the introducer.

BRIEF DESCRIPTION OF THE DRAWINGS

The above and other objects and advantages of the present invention will become more apparent and better understood from the following description, claims and drawings in which:

FIGS. 4-6 are top views of the valve shown in FIG. 2 describing respectively each of the three operating positions of the valve.

DETAILED DESCRIPTION OF THE DRAWINGS

Figure 1:
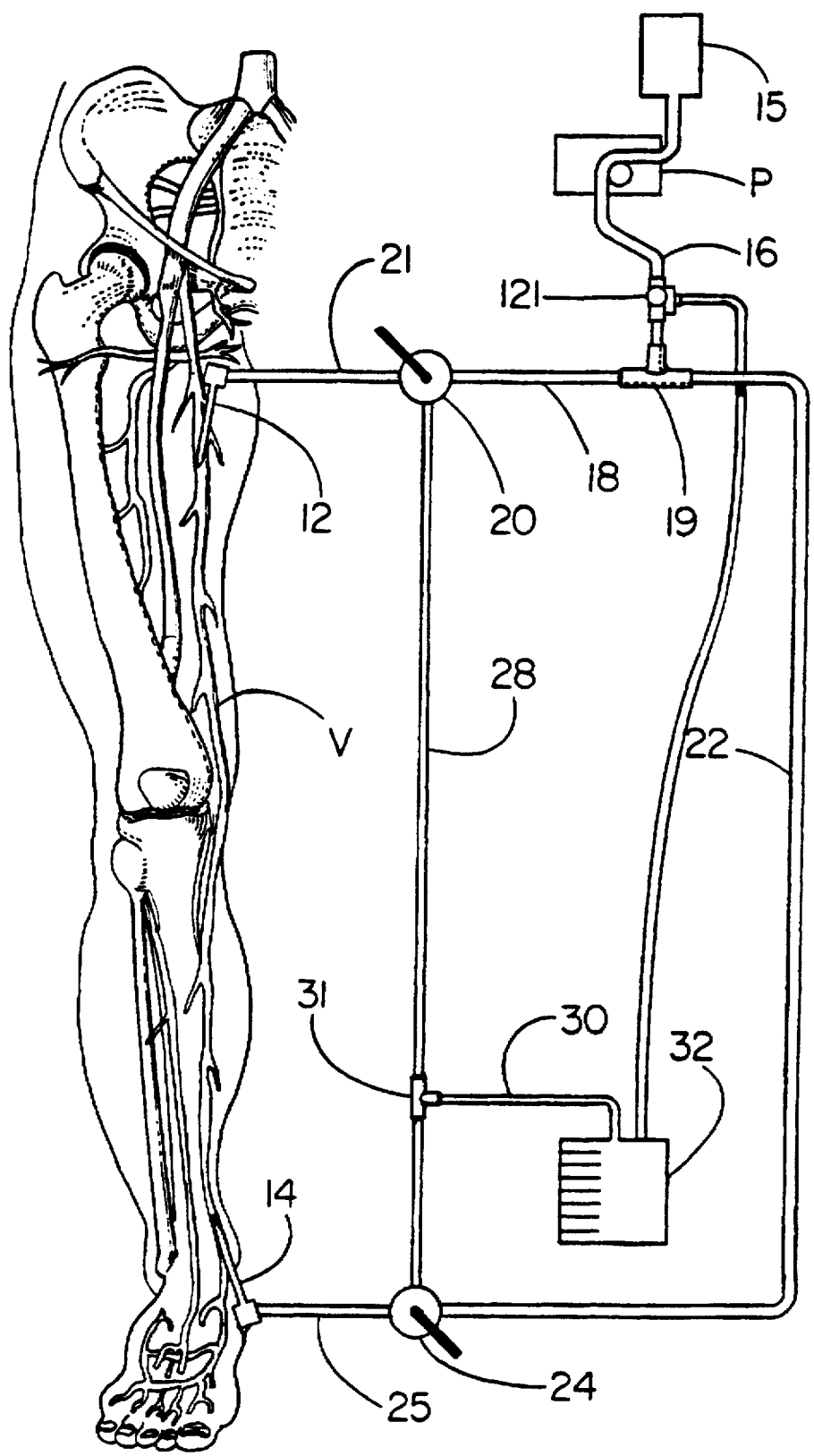
FIG. 1 is a schematic diagram showing one embodiment of the angioscopic irrigation system of the present invention connected to the saphenous vein of a patient undergoing in situ bypass.

Various surgical procedures, such as laparoscopic surgery and angioscopic procedures, require irrigation of the surgical site so that the surgeon is afforded an unobstructed view of the surgical site, free of blood and other material.

Since its introduction in about 1962, the operative technique for in situ saphenous vein bypass (ISVB) has undergone modification and improvement due to the development of new technology and surgical instruments, such as the introduction of angioscopy, which has improved graft patency and limb salvage. In this procedure, two incision techniques are generally utilized to complete bypass and revasculization procedure. One technique involves placing incisions in the groin area over the sapheno-femoral junction and the proximal and distal ends of the saphenous vein are exposed. The entire length of the saphenous vein is then exposed. Medical literature indicates that there is a 33% to 40% wound healing morbidity rate which can significantly increase the length of a hospital stay or compromise the graft in some cases.

The second technique is termed a "semi-closed" procedure in which small incisions are made in the groin area and below the knee with stab wound incisions being made along the leg to access tributaries for ligation. This latter procedure has been shown to reduce wound healing complications thereby improving patient recovery. In this procedure, angioscopy is one technique to assist in completing a semi-closed technique. The use of the patient's autologous saphenous vein, in place, as a bypass conduit to an occluded femoral artery is commonly known as in situ saphenous vein bypass. During the procedure, the venous valves are disrupted and the tributaries ligated to enable the saphenous vein to be used as a suitable arterial bypass conduit. The proximal and distal saphenous vein is dissected from the femoral vein both medially and marginally and, after preparation, anastomitized to the artery.

When performing these procedures, the surgeon must ensure complete valve disruption and identify location of tributaries and angioscopic visualization is one procedure utilized in the vein for these purposes. Proximal and distal introducer sheaths are inserted and affixed at each end of the vein and connected by tubing to an irrigation system. The irrigation tubing set is connected to an infusion pump. A valvulotome is inserted through the hemostatic port of the distal introducer sheath. The infusion pump will be placed in the bolus mode which establishes a flow rate of approximately 100 to 250 milliliters per minute. Irrigation at this rate will quickly clear the field of view and minimize fluid volume and pressure infused into the patient by venting the blood and irrigation solution to a collection bag. The angioscopic irrigation procedure allows the surgeon to determine valve, tributary and tortuosity locations as the valvulotome catheter is inserted prior to valvulotomy. Once the field of view is clear, the surgeon then places the infusion pump into a maintenance mode of operation with a typical flow rate of about 40 to 100 milliliters per minute.

With current techniques the angioscopic irrigation catheter is typically passed from proximal to distal in the vein which requires substantial fluid volume and longer times to clear and maintain the field of view. This does not allow viewing of the entire vein until after valvulotomy is completed. Further, current systems do not permit simultaneous irrigation at both the proximal and distal sites and does not adequately vent fluid, placing additional fluid load stress on the patient. Accordingly, the present invention was developed to overcome these deficiencies as it allows bi-directional flow for better visualization and reduces venous and patient stress due to high irrigation fluid pressure and volume allowing inspection of an entire vein prior to valvulotomy.

In FIG. 1, which shows an embodiment of the irrigation system of the invention, the proximal and distal ends of the saphenous vein has been dissected from the femoral vein. Proximal and distal introducer sheaths 12 and 14 are shown inserted and affixed to opposite ends of the vein "V". The sheaths may be conventional introducer sheaths of the type available from Burron, Division of B. Braun, or may be the type more fully described3 with reference to FIGS. 8a, 8b, 9a and 9b. A bag or container of irrigation solution 15 is connected to the inlet of pump "P", having outlet 16. Outlet 16 connects to tee 19 and is directed from one outlet of the tee 19 to introducer sheath 12 via line 21 across direction control switch or valve 20. Output 16 is also connected via tee 19 to the lower or distal introducer sheath 14 via line 22, across valve 24 and through line 25. Valves 20 and 24 each have a second output port which are interconnected by line 28. Line 28 is connected by means of tee 31 and line 30 to fluid collection bag 32. The valves 20 and 24 may be three-way stopcocks (No. B1000062) of the type manufactured by Burron, Division of B. Braun Medical.

The system also should include pressure relief valve 121 which is pre-set to direct fluid to the drain bag 32 or other venting location if pressure exceeds a predetermined level to prevent venous damage.

As the catheter of the angioscopic assembly is advanced from distal to the proximal locations, the system of the present invention allows irrigation flow to be directed from the pump outlet 16 through line 22 and across valve 24 to the distal introducer sheath 14 and through the vein to the proximal introducer sheath. The return or vent flow from the proximal introducer sheath 12 is directed via line 21 to valve 20 which is positioned to direct flow to lines 28 and 30 into collection bag 32. The initial flow rate to clear the field is a bolus flow rate of approximately 100–250 milliliters per minute. As the initial bolus rate is maintained, irrigation fluid is allowed to vent until clear fluid is observed at the proximal vent and a clear angioscopic field is established. These observations indicate the entire length of the vein is filled with irrigant and no blood is present to obscure the field of view. At this time, the infusion pump is lowered to a maintenance flow rate of approximately 40–100 milliliters per minute.

Irrigation flow may also be directed at this time to both the proximal and distal introducer sheaths 12 and 14 . Simultaneous flow to both the proximal and distal ends of the vein "V" will maintain a positive venous pressure preventing tributary blood flow from entering the vein and obscuring the field of view. Simultaneous introduction of irrigation fluid at both the distal and proximal ends can be accomplished by positioning the valves 20 and 24 so that flow is directed to both introducer sleeve locations. No vent flow occurs in this condition and the irrigation fluid, normally saline solution, is absorbed by the patient.

When performing this procedure, an introducer head may be exchanged for a cutting head after exiting the hemostatic port of the introducer sheath at the proximal vein end. One such device is the GORE EZE-SIT® Valvulotome available from W. L. Gore & Associates, Inc. of Flagstaff, Ariz. The cutting head is drawn back into the proximal end of the vein and irrigation flow is simultaneously introduced from the proximal to the distal end of the vein to clear the field of view and to close the venous valve for cutting. At the same time, the distal valve 24 is positioned to direct venting fluid flow to the collection bag 32. Once the valvulotomy is completed, the angioscope may be passed in both proximal and distal directions in the vein, switching fluid flow to optimize clearing and maintenance of a clear field of view. Selective operation of the valves 20 and 24 permit this flow reversal.

In summary, the irrigation system of the present invention provides three functions:

(1) The system provides for distal to proximal irrigation flow while venting and drawing from the proximal vein end;

(2) The system provides simultaneous flow into both the proximal and distal ends of the vein resulting in a hydrostatically pressurized vein which prevents blood from entering the the vein from the venous tributaries, thereby maintaining a clear field of view; and (3) The system provides for proximal to distal irrigation flow while venting or draining fluid from the distal end of the vein for closing venous valves and for viewing during the valvulotomy procedure and inspection of the vein after valvulotomy.

Figure 2:
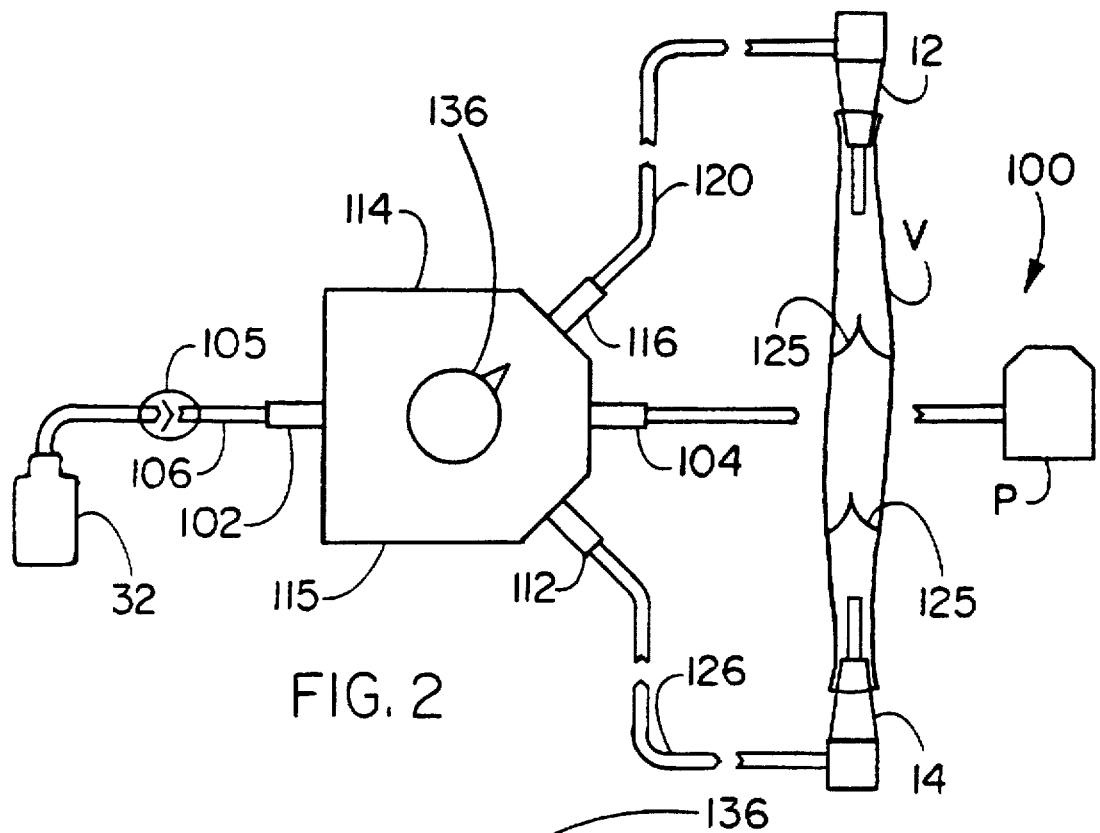
FIG. 2 is a schematic view of an alternate embodiment of the irrigation system which includes a single control valve for selectively directing irrigating fluid to the desired irrigation location and for directing return irrigation flow to a collection bag.
Figure 3:
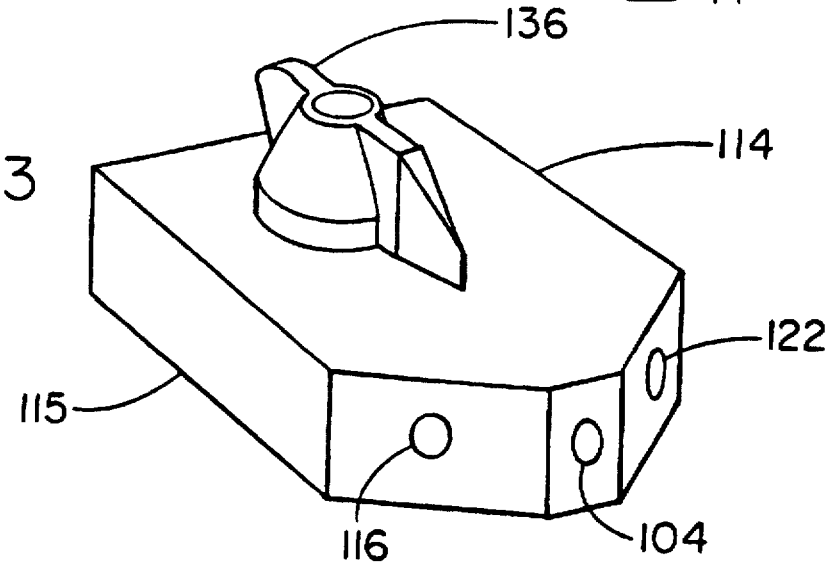
FIG. 3 is a perspective view of the valve shown in FIG. 2.

While the system shown in FIG. 1 is simple and effective, it requires the operation of two flow control valves, valves 20 and 24. In many applications, it is more convenient to have the flow logic integrated within a single valve unit. Accordingly, referring to FIG. 2, an irrigation system complete with introducer sheaths, catheters, tubing, fluid collection container and valving is shown which allows the surgeon to control the irrigation flow and direction by manipulating a single flow control device. This system, generally designated by the numeral 100, includes a pump "P" connected to a valve 114 at inlet port 104. The valve has a drain or outlet port 102 which is connected by conduit 106 to a collection bag or container 32. Preferably the collection container is provided with calibrations which allow medical personnel to better monitor the fluid volume collection. A check valve 105 may be interposed in line 106 to prevent siphoning of fluid from the collection bag 32. Alternatively, the check valve may not be needed if collection bag 32 is placed at a height approximately equal to the level of the patient. The valve 114 has a body 115 which has a first outlet port 116 (also referred to as proximal port 116) which is connected to proximal introducer sheath 12 via conduit 120. A second outlet port 122 (also referred to as distal port 122) leads to a distal introducer sheath 14 via conduit 126. These lines may be any suitable medical grade conduit such as silicon rubber tubing. The vein "V" is schematically represented and shown extending between the proximal and distal introducer sheaths. Several venous valves 125 are shown which are bicuspid valves in which the cusps coapt in competent valves.

Figure 7:
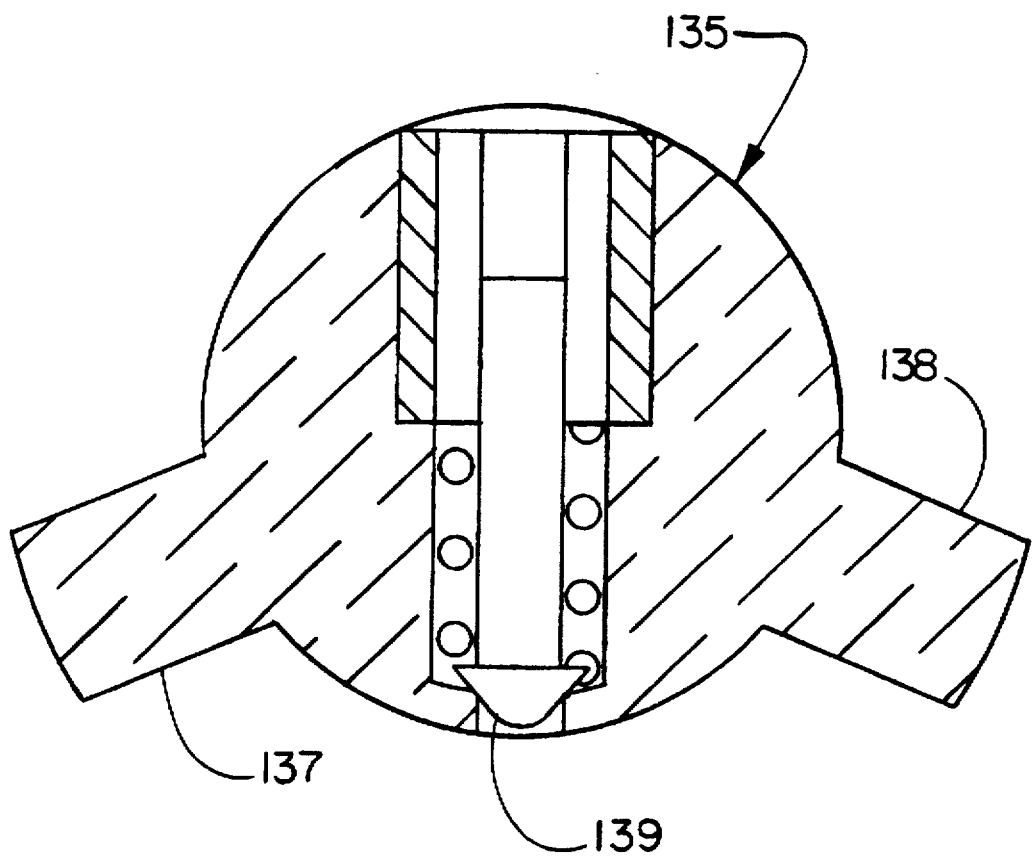
FIG. 7 describes the valve spool.

Referring to FIGS. 3 to 7, the valve body 115 has a valve bore 130 which receives a valve spool 135. Valve spool 135 is rotatable within the bore by means of a control or selector knob 136 the rotation of which is restricted to about 90° for the valve body geometry depicted. Preferably valve 114 is provided with selector knobs on both sides of valve body 115; this allows the valve body to be located either side up depending on whether the procedure is being performed on the left or right leg of a patient. For example, FIG. 2 describes the valve 114 positioned for the procedure as performed on a right leg allowing the valve and associated lines to be placed to the right of the patient; FIGS. 3-6 alternatively show the opposite side of the valve placed upward as it would be for a left leg procedure. Valve spool 135 includes barriers 137 and 138 which divert irrigation fluid from the inlet port to the desired outlet ports as controlled by position selector knob 136. FIG. 4 describes the valve 114 with spool 135 in a first position wherein it is positioned to direct irrigation fluid from inlet port 104 out to proximal port 116; this position also directs fluid that has flowed through vein "V" from the distal port 122 to drain port 102. FIG. 5 describes the valve 114 with spool 135 in a second position in which it is positioned to direct fluid from inlet port 104 out to both proximal port 116 and distal port 122 simultaneously for maximum clear field of view; in this position drain port 102 is only connected to inlet port 104 by pressure relief valve 139 in the center of valve spool 135 which allows fluid to flow out to drain port 102 only in the event of an overpressure condition. Under normal pressure conditions at this valve setting, fluid flows into both the proximal and distal introducers 12 and 14 from proximal port 116 and distal port 122 respectively, with the flow being absorbed by the venous tributaries. FIG. 6 shows the valve spool 135 positioned in a third position to allow flow from inlet port 104 to distal port 122 and on to distal introducer 14; flow continues through vein "V" out to proximal introducer 12 and through proximal port 116 to drain port 102 and collection bag 32. FIG. 7 is a top view of valve spool 135 which includes pressure relief valve 139.

Figure 8A:
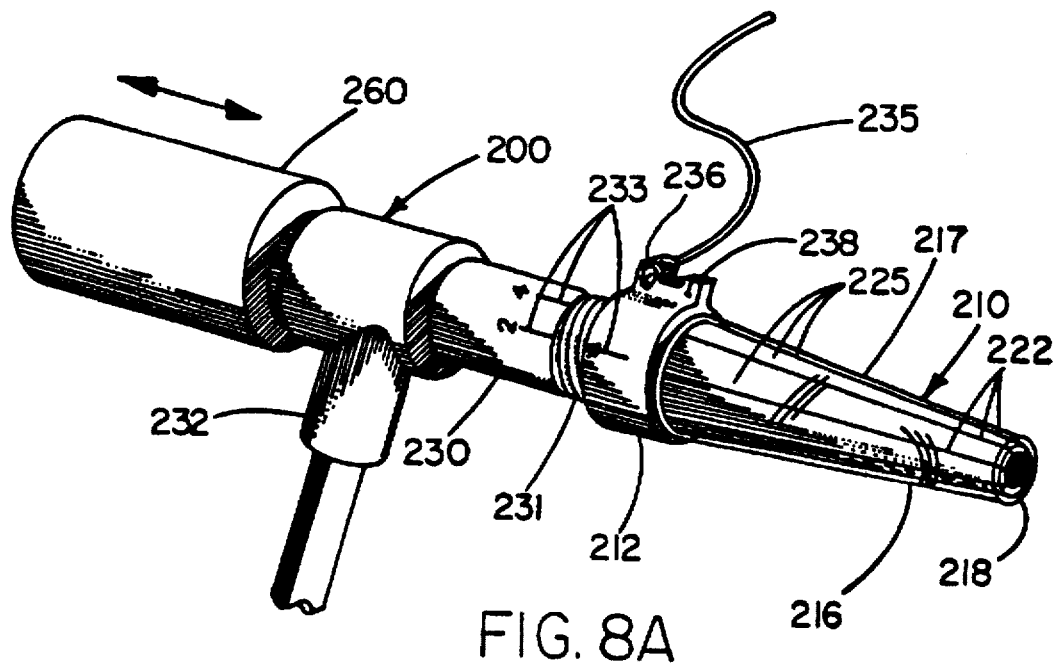
FIGS. 8A and 8B describe perspective views of an introducer which may be used with the irrigation system of the present invention.
Figure 8B:
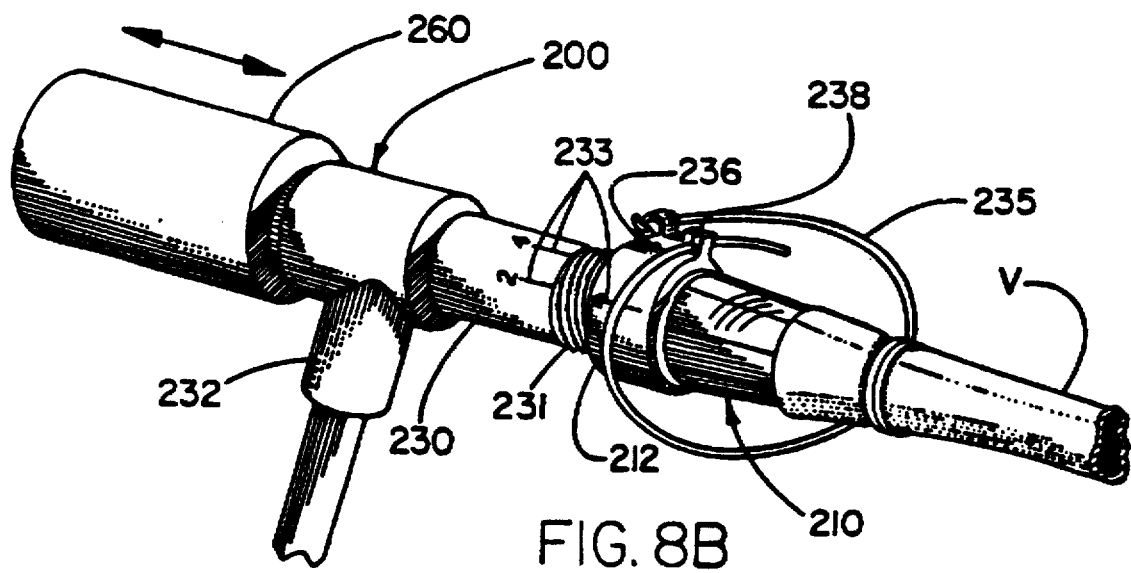

In FIGS. 8A, 8B, 9A and 9B, an intravenous introducer sheath is shown which provides advantages over current design introducer sheaths. While current design introducer sheaths may be used with the irrigation system of the present invention, the introducer sheath shown in these figures is preferred because it is universal having a tip adjustable to be accommodated by various vein sizes. Conventional introducer sheaths are provided in various sizes, and the surgeon must select the appropriate introducer required for the particular French diameter of the vein. Further, no provision is made in current introducer sheath designs to allow passage of sharps through the hemostatic port without damaging the sealing grommet. The introducer sleeve shown in FIGS. 8A, 8B, 9A and 9B is generally designated by the numeral 200 and includes an expandable tip 210. The expandable tip 210 has an annular collar 212 at the proximal end and a forwardly extending hollow end portion 216. The end 216 has a rounded hollow tip 218 for insertion into a vein. As seen in these figures, the end has a plurality of slits 222 which form a plurality of axial extending flexible segments 225 which extend from adjacent the collar to the tip. The end may be formed from various medical grade materials which allow the introducer to be kink resistant and sufficiently rigid to facilitate insertion in a vein. End 216 should be provided with compliant covering 217 in order to make slits 222 liquidtight. Medical grade silicon elastomer is anticipated to be a suitable material for covering 217. The materials from which the introducer sleeve 200 is made may be selected for single use or may be selected to allow the introducer sheath or some of its components to be sterilized and re-used. The diameter of the rounded hollow tip 218 in an unexpanded condition is selected to correspond to the size of the smallest vein size normally encountered which is about 2 millimeters (3 French). The expandable tip 210 is assembled to coupling 230 (which includes fluid port 232) by means such as threads 231. By tightening the expandable tip 210 to coupling 230 via threads 231, the end 234 of coupling 230 increasingly interferes with the inner surface of axial extending flexible segments 225 thereby forcing them open and increasing the diameter of rounded hollow tip 218. FIG. 8B shows the introducer sleeve 200 fitted into the lumen of a vein "V". It is shown secured by line 235 which is affixed at one end to introducer sleeve 200 at line retainer 236 via a hole 237 through line retainer 236. The other end of line 235 is quickly and conveniently retained in slot 238 of line retainer 236. Line 235 is preferably a resilient and stretchable material such as silicone rubber.

Note the coupling is calibrated with indicia 233 indicating, as for example, the diameter (French or in millimeters) of the tip as the collar is positioned at these locations along the coupling. These indicia may be also be used as an aid in determining vein diameter for proper tool size selection. Alternatively, indicia may be provided as transversely oriented indicator marks (not shown) on the exterior surface of expandable tip 210 at appropriate locations along the length of expandable tip 210.

Figures 9A, 9B:
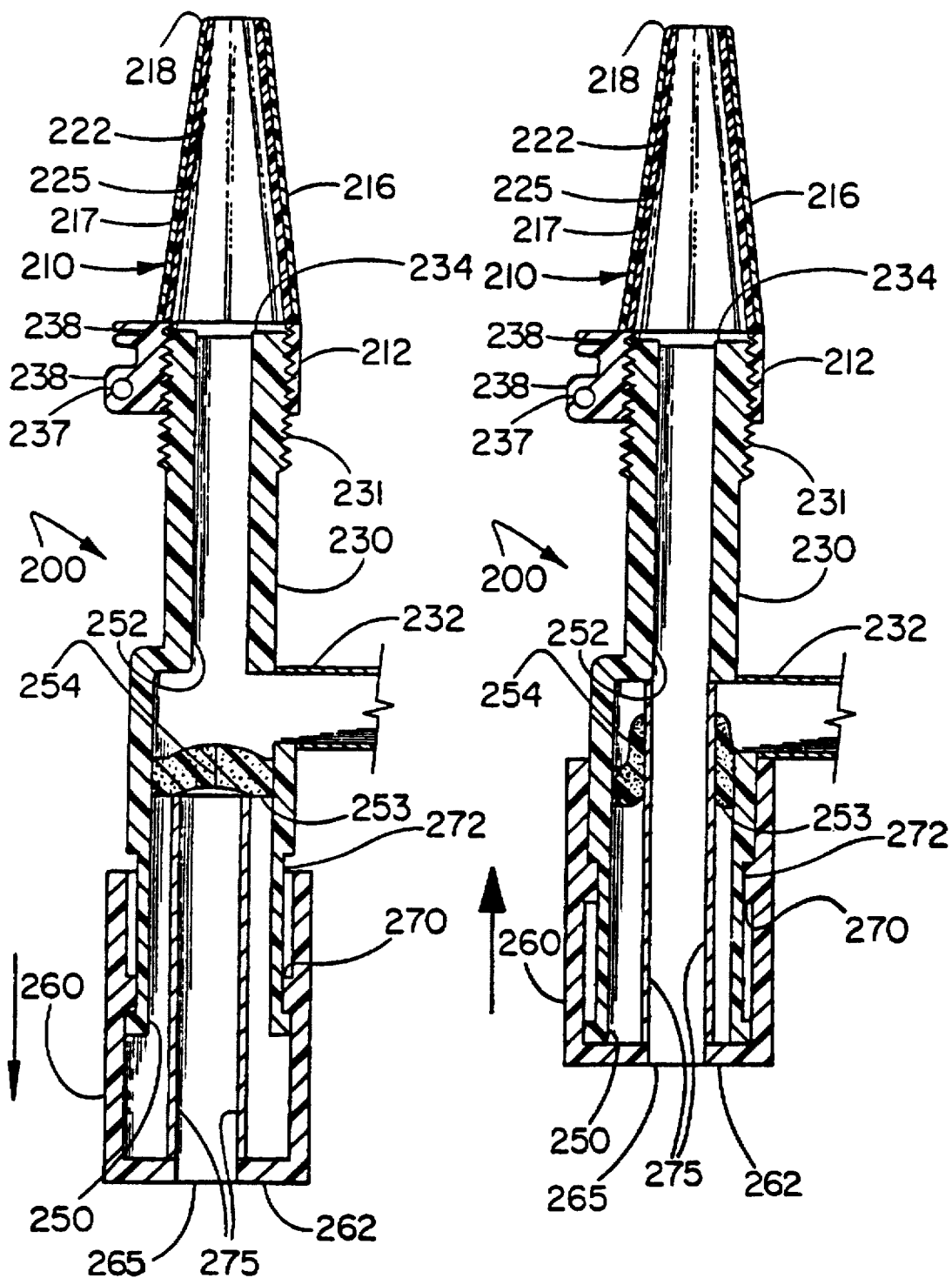
FIGS. 9A and 9B describe longitudinal sections of the introducer.

As best seen in the longitudinal cross sections of FIGS. 9A and 9B, the left end of the coupling 230 defines an axial opening 250 which communicates with the lumen 252 in the coupling 230. The opening 250 receives an elastomeric sealing member 253 such as a disk of silicon rubber which is slit to provide a hemostatic port 254. One problem, as indicated above, is that shapes passed through the hemostatic port 254 may cause the resilient sealing member 253 to be damaged reducing its effectiveness. Accordingly, an annular cap 260 having an outer body is engageable over the end of the coupling 230 opposite expandable tip 210. The cap 260 has inwardly extending projections 270 which are received in axial guide slots 272 in the exterior of the coupling to facilitate sliding movement of the annular cap 260 relative to the coupling 230. The annular cap 260 has an annular end 262 which defines a concentric opening 265. A tubular sleeve 275 extends inward axially, which, as the cap is moved inwardly, will extend inwardly a sufficient distance to engage, open and protect the resilient seal 253.

In a typical valvuolotmy procedure, when a catheter is inserted into tubular sleeve 275 of the proximal introducer 12, it is passed through the hemostatic port 254 to enable exchange of the blunt introducer head or cutter head with another sharp valve cutter head. When the heads are exchanged, the protective introducer cap 260 is moved into the position shown in FIG. 9B to protect the hemostatic seal. The tubular sleeve 275 prevents cutting of the hemostatic seal 254 when drawing the catheter and cutterhead back into the vein for the valvulotomy process.

Once the cutter head and catheter are withdrawn inside the vein, the cap 260 is moved axially away from the expandable tip 210 to move the sleeve from its protective position in the hemostatic port. The seal 253 is exposed and the proximal fluid valve is then placed in the irrigation position, enabling fluid flow from the proximal to the distal ends of the vein to both close the venous valves for cutting and clearing the field of view. At the same time, the distal fluid valve is placed in the vent position to collect solution after the valvulotomy is completed. The angioscope may be passed proximal and distally switching fluid flow proximally and distally to optimize clearing and maintenance of field of view.

From the foregoing, it is seen that the present invention provides an improved irrigation system including a unique selector valve for selectively directing irrigation flow to the surgical site and controlling the flow direction and the direction of the fluid to a collection device. The present invention also provides a unique introducer sheath which is expandable allowing it to be used with a range of sizes of veins. The introducer sheath also has a unique cap to protect the elastomeric seal at the hemostatic port.

While the principles of the invention have been made clear in the illustrative embodiments set forth above, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

While the above specification is directed primarily to the use of the present invention to excise valves from veins, it should be understood that the present invention may have other useful applications. For instance, the present invention may be useful for removing obstructions in a vein or artery. As such, the present invention is believed to have use in all forms of body conduits.

We claim:

1. An irrigation system for irrigation of a surgical site comprising:
   (a) a fluid pressure source having an inlet and an outlet;
   (b) a first fluid conduit connected to said outlet and terminating at a first location;
   (c) a second fluid conduit connected to said outlet and terminating at a second location;
   (d) a first selector valve in said first fluid conduit, said first selector valve having a first position establishing fluid communication with said first location and having a second by-pass position communicating with a by-pass outlet;
   (e) a second selector valve in said second fluid conduit, said second selector valve having a first position establishing fluid communication with said second location and having a by-pass position communicating with a by-pass outlet;
   (f) first and second introducer sheaths at said first and second locations, respectively;
   (g) a by-pass fluid conduit interconnecting said by-pass outlets; and
   (h) a fluid collection container connected communicating with said by-pass conduit whereby said first and second valves are operable to simultaneously provide bi-directional fluid flow to both of said introducer sheaths or selectively direct fluid flow to either introducer sheath and direct return flow via the other introducer sheath to said fluid collection container.

2. The system of claim 1 wherein said introducer sheaths include a hemostatic port.

3. The system of claim 1 wherein said first and second selector valves are integrally formed within a single valve body having a valve spool operable by a selector to selectively direct fluid to said introducer sheaths and to said fluid collection container.

4. The system of claim 1 further including anti-siphon means for preventing flow from said fluid collection container.

5. The system of claim 4 wherein said anti-siphon means comprises one-way valve means.

6. The system of claim 1 wherein said fist and second fluid conduits include pressure regulating means.

7. A medical irrigation system comprising an irrigation fluid pressure source connected to at least one fluid control valve connected to a proximal introducer sheath and a distal introducer sheath, wherein the proximal introducer sheath is at a proximal location on a body conduit for transport of irrigation fluid through the body conduit and the distal introducer sheath is at a distal location on the body conduit for transport of the irrigation fluid through the body conduit, wherein irrigation fluid flow from the irrigation fluid pressure source through the system is directed via the at least one fluid control valve which provides first, second and third functions each of which is individually selected by controlling the at least one fluid control valve wherein:

a) said first function provides distal to proximal irrigation flow with the irrigation fluid introduced to the body conduit through the distal introducer sheath and vented from the body conduit through the proximal introducer sheath;

b) said second function provides proximal to distal irrigation flow with the irrigation fluid introduced to the body conduit through the proximal introducer sheath and vented from the body conduit through the distal introducer sheath; and c) said third function provides simultaneous flow of the irrigation fluid into both the proximal and distal introducer sheaths.

8. An irrigation system according to claim 7 wherein the at least one fluid control valve is a single fluid control valve.

9. An irrigation system according to claim 7 wherein the at least one fluid control valve is two fluid control valves.

10. An irrigation system according to claim 7 wherein said fluid irrigation provides a clear field of view for an angioscope.

* * * * *